United States Patent
Rauh et al.

(10) Patent No.: US 10,449,021 B2
(45) Date of Patent: Oct. 22, 2019

(54) PROSTHETIC PREFORM FOR PRODUCING A DENTAL PROSTHETIC BODY

(71) Applicant: Vita Zahnfabrik H. Rauter GmbH & Co. KG, Bad Saeckingen (DE)

(72) Inventors: Wolfgang Rauh, Bad Saeckingen (DE); Urban Christen, Bad Saeckingen (DE); Franz Egle, Bad Saeckingen (DE); Eva Kerschensteiner, Bad Saeckingen (DE)

(73) Assignee: VITA ZAHNFABRIK H. RAUTER GM BH & CO. KG, Bad Saeckingen (DE)

( * ) Notice: Subject to any disclaimer, the term of this patent is extended or adjusted under 35 U.S.C. 154(b) by 84 days.

(21) Appl. No.: 14/894,025

(22) PCT Filed: May 21, 2014

(86) PCT No.: PCT/EP2014/060478
§ 371 (c)(1),
(2) Date: Nov. 25, 2015

(87) PCT Pub. No.: WO2014/191286
PCT Pub. Date: Dec. 4, 2014

(65) Prior Publication Data
US 2016/0128811 A1    May 12, 2016

(30) Foreign Application Priority Data
May 27, 2013  (EP) .................... 13169349

(51) Int. Cl.
*A61C 13/20*  (2006.01)
*A61C 13/01*  (2006.01)
(Continued)

(52) U.S. Cl.
CPC ............. *A61C 13/20* (2013.01); *A61C 13/01* (2013.01); *A61C 13/34* (2013.01); *A61C 13/0022* (2013.01)

(58) Field of Classification Search
CPC ....................................................... A61C 13/01
(Continued)

(56) References Cited

U.S. PATENT DOCUMENTS 5,151,044 A      9/1992  Rotsaert
8,308,480 B2 *  11/2012  Bublewitz ............ A61C 9/0006
                                                                 433/37
(Continued)

FOREIGN PATENT DOCUMENTS

DE     102007014985 A1    10/2008
DE     202012100359 U1     3/2012
(Continued)

OTHER PUBLICATIONS

International Search Report dated Aug. 29, 2014 for PCT application No. PCT/EP2014/060478.

*Primary Examiner* — Laura C Powers
(74) *Attorney, Agent, or Firm* — Ohlandt, Greeley, Ruggiero & Perle, LLP

(57) ABSTRACT

To produce a dental prosthetic body for an upper or lower jaw prosthesis, a prosthetic preform is provided, the prosthetic preform having approximately the same shape as the prosthetic body. As a result, a high quality prosthetic body can be produced and customized, for example, by milling the prosthetic prebody.

18 Claims, 5 Drawing Sheets

(51) Int. Cl.
*A61C 13/34* (2006.01)
*A61C 13/00* (2006.01)

(58) Field of Classification Search
USPC .................................... 423/171; 428/542.8
See application file for complete search history.

(56) References Cited

U.S. PATENT DOCUMENTS

| | | | |
|---|---|---|---|
| 2002/0127264 A1* | 9/2002 | Felt ...................... | A61B 17/562 424/423 |
| 2004/0241614 A1* | 12/2004 | Goldberg ............ | A61C 13/0003 433/202.1 |
| 2008/0241798 A1 | 10/2008 | Holzner et al. | |
| 2009/0291416 A1* | 11/2009 | Brunson .............. | A61C 9/0006 433/215 |
| 2010/0219546 A1* | 9/2010 | Puttler .................... | A61C 7/00 264/16 |
| 2010/0255053 A1* | 10/2010 | Savage-Erickson .... | A61L 27/12 424/423 |
| 2010/0297580 A1* | 11/2010 | Niewiadomski ... | A61C 13/0009 433/167 |
| 2011/0039974 A1* | 2/2011 | Vekoerrer ............ | A61K 6/0008 523/115 |
| 2011/0268525 A1 | 11/2011 | Karpowitz et al. | |
| 2012/0107771 A1 | 5/2012 | Hrenak | |
| 2013/0101962 A1 | 4/2013 | Howe | |
| 2014/0317930 A1 | 10/2014 | Klingenburg et al. | |
| 2014/0377718 A1* | 12/2014 | Korten ............... | A61C 13/0022 433/218 |

FOREIGN PATENT DOCUMENTS

| | | |
|---|---|---|
| DE | 102011118320 A1 | 5/2013 |
| WO | 2011124474 A1 | 10/2011 |
| WO | 2013117540 A1 | 8/2013 |

* cited by examiner

PROSTHETIC PREFORM FOR PRODUCING A DENTAL PROSTHETIC BODY

BACKGROUND

1. Field of the Disclosure

The disclosure relates to a prosthetic preform for producing a dental prosthetic body, with the prosthetic body serving to receive teeth. The prosthetic bodies are removable dentures, in particular in the form of full prostheses or partial prostheses.

2. Discussion of the Background Art

Nowadays, prosthetic bodies, in which individual teeth are fixed, are produced manually and individually for each patient. To this end, typically, a polymer material is introduced into a corresponding mold, based on an impression of a jaw. It is thus necessary to make patient-individualized molds for the lower and upper jaws in order to be able to produce a respective prosthetic body for the lower jaw and the upper jaw. This is an extremely time-consuming and costly process.

It is an object of the present disclosure to provide for an economic production of such prosthetic bodies.

SUMMARY

It is a preliminary consideration of the disclosure to produce prosthetic bodies from a prosthetic preform by material-removing processes, in particular by milling. This could be achieved by using for example circularly cylindrical bodies, so-called round blanks. The use of such round blanks has the advantage that they can be made with a very high quality of material which is constant in particular over the entire volume of the round blank. Specifically, such round blanks may be produced with a constant density and preferably also free from residual polymer. On the other hand, the use of round blanks of circularly cylindrical shape have the disadvantage that a large amount of material hast to be removed. This also results in high tool wear, as well as in long production times.

According to the disclosure a prosthetic preform is therefore proposed, instead of a circularly cylindrical round blank, which preform approximates the shape of the prosthetic body to be manufactured. Specifically, the prosthetic preform approximates the prosthetic body to be manufactured such that a saving of material is achieved that is in the order of more than 20%, preferably more than 30%, particularly more than 40%, and particularly preferred more than 50%. Particularly high savings of material of preferably more than 50%, in particular even more than 55%, may be achieved with prostheses for the lower jaw, since a portion in contact with the palate is not worked out. The above indicated features are to be understood in comparison with a circularly cylindrical round blank. Such a conventional circularly cylindrical round blank has no indentation and/or recesses. It is a circularly cylindrical solid body. The saving of material preferred according to the disclosure may be realized for example by pressing indentations into the prosthetic preform. This is advantageous in that less material has to be removed during a subsequent material-removing processing. Further, the production of the corresponding prosthetic preforms of the present disclosure may be realized using suitable molds so that, thereby, material saving is possible. For example, a standard round blank has a material volume of about 247 cm$^3$. A prosthetic preform of the present disclosure for an upper jaw may have a material volume of about 138 cm$^3$ so that a saving of material of about 44% can be achieved. Such a preform of the present disclosure for a lower jaw preferably has a volume of only about 103 cm$^3$ so that even a saving of material of about 58% can be achieved as compared with a standard round blank.

In another preferred embodiment the prosthetic preform of the present disclosure has a material volume of less than 200 cm$^3$, particularly less than 180 cm$^3$, preferably less than 150 cm$^3$, and particularly preferred less than 125 cm$^3$.

The prosthetic preform is preferably made of polyamide, polyacrylate (such as polymethyl methacrylate), polycarbonate, polyepoxy and/or polyetherketone (for example PEEK and PAEK), all with or without fillers.

The production of the prosthetic body, into which the teeth are set, is performed preferably by removal of material, in particular by milling and specifically by CAD/CAM milling techniques. Manual processing is not required or, if at all, only in the form of minor post-processing.

Preferably, the prosthetic preform has a circularly cylindrical basic shape, wherein at least one recess, indentation, notch or the like is provided in at least one end face to obtain the approximated shape. The prosthetic preform may for example also have polygonal base area instead of a circular base area. The design of the outer surface of the basic shape depends in particular on the handling by the processing machines. In particular, the outer surface side of the basic shape may be designed such that the prosthetic preform can be received in a simple and positionally accurate manner in a processing machine, such as a milling machine. For this purpose, the outer surface may for example also be provided with protrusions, notches, recesses or the like for adjustment in the work piece holder.

In a particularly preferred embodiment the prosthetic preform has a main body which, after processing, forms the individualized prosthetic body. Further, it is preferred that the prosthetic preform has a retaining body in addition to the main body. The retaining body serves in particular to receive the prosthetic preform in the processing machine. In this regard, it is particularly preferred that the retaining body surrounds the main body at least in part, preferably completely. Preferably, the retaining body annular in shape and surrounds the main body.

In a further preferred embodiment the prosthetic preform may also be designed such that the portion forming the main body is raised and is connected with a disc-shaped element. Here, the disc-shaped element forming the retaining body may surround the main body completely or partly. By designing the retaining body as a disc-shaped element, an additional saving of material can be achieved, since the disc-shaped element has a smaller thickness than an annularly shaped retaining body. The retaining body may thus have a height or thickness that is smaller, overall or in part, than that of the main body which, after processing, forms the individualized prosthetic body.

In another preferred embodiment the main body is connected with the in particular annular or disc-shaped retaining body via webs. This is advantageous in that the main body is well accessible for the processing tool for producing the prosthetic body and in that, as such, a facilitated processing also of side surfaces of the prosthetic body can be performed. Due to the connection between the main body and the retaining body via webs, passage openings are formed between the webs so that, in particular in these regions, a processing of side surfaces of the main body can be performed in a simple manner to produce the prosthetic body.

It is particularly preferred to provide different prosthetic preforms. Specifically, different prosthetic preforms may be provided for the production of a prosthetic body for the upper jaw and the lower jaw, respectively. Besides that, different sizes for different jaw sizes are possible as well. Specifically, it is thus possible to provide a plurality of different prosthetic preforms adapted to frequent marginal conditions, so that a prosthetic preform may be selected that is as close as possible to the anatomic requirements of a patient. This has the advantage that little processing must be done, whereby lower costs are caused and, further, the waiting time is shortened for the patients. In this regard, it is particularly preferred to define groups of patients for which a respective prosthetic preform is then provided.

For forming a prosthetic body for a lower jaw denture, the main body preferably is substantially U-shaped. For forming a prosthetic body for an upper jaw, the substantially U-shaped form is supplemented by an interposed palate contact element.

In a preferred embodiment the design of the retaining body may not only be adapted to the processing machine or the workpiece holder of the processing machine, but in particular also vary in height. Thus, the retaining body may at least have the same height as the main body so that the main body is arranged in particular completely in the retaining body annularly surrounding the main body. Likewise, in particular for material saving purposes, the retaining body may be flat and may thus have a height clearly smaller than the main body.

The following is a detailed description of the disclosure with reference to preferred embodiments and to the accompanying drawings.

DETAILED DESCRIPTION OF THE PREFERRED EMBODIMENT

Figure 1A:
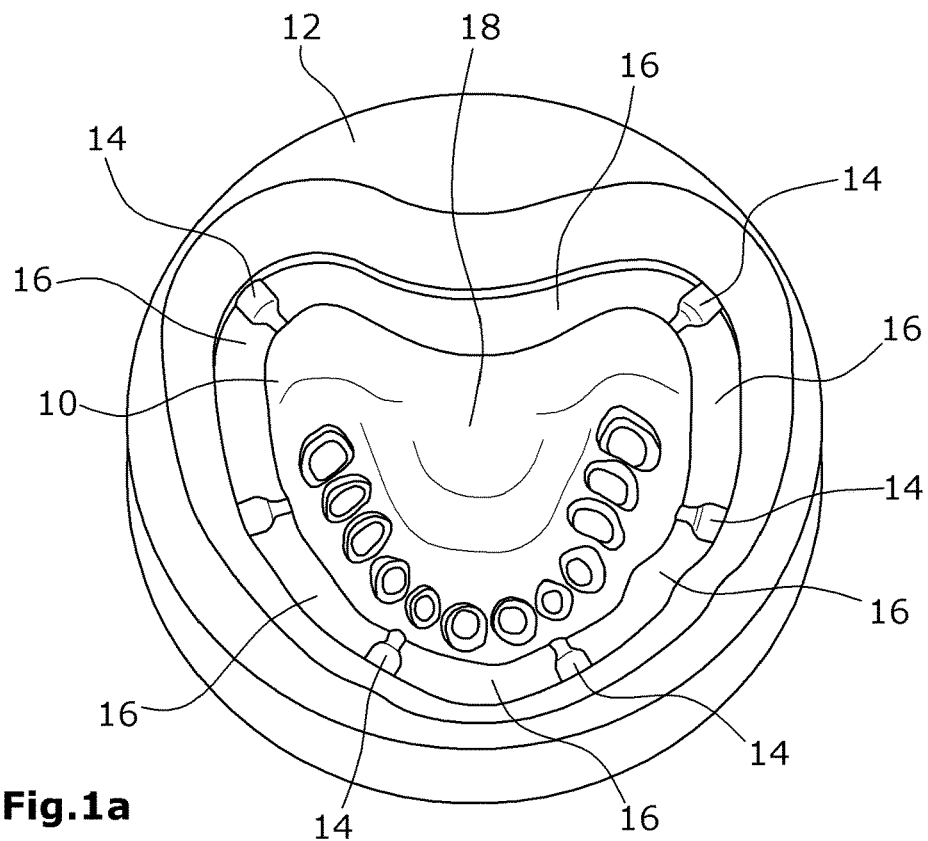
FIG. 1a illustrates a first preferred embodiment of an at least partly processed prosthetic preform for an upper jaw denture.

In the four different preferred embodiments illustrated in FIGS. 1-4, which only represent preferred example of at least partly processed prosthetic preforms of the present disclosure, similar or identical components are identified by the same reference numerals.

Figure 1B:
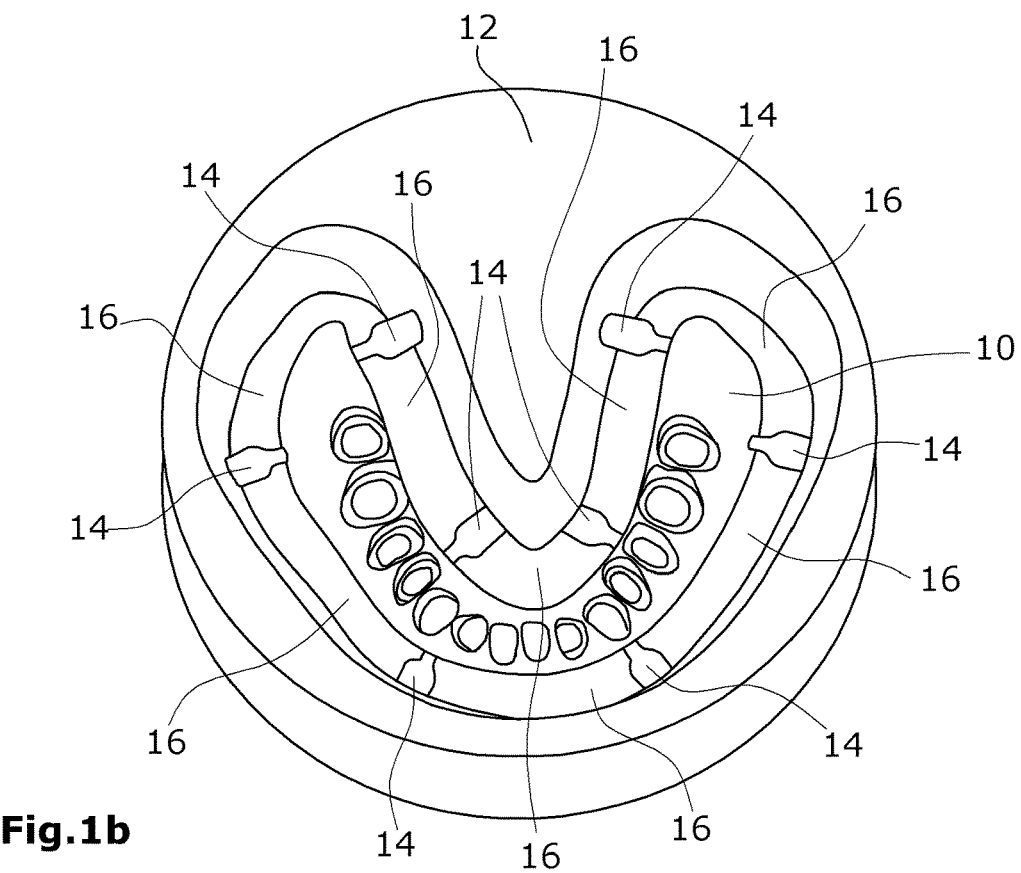
FIG. 1b illustrates a first preferred embodiment of an at least partly processed prosthetic preform for a lower jaw denture.
Figure 3A:
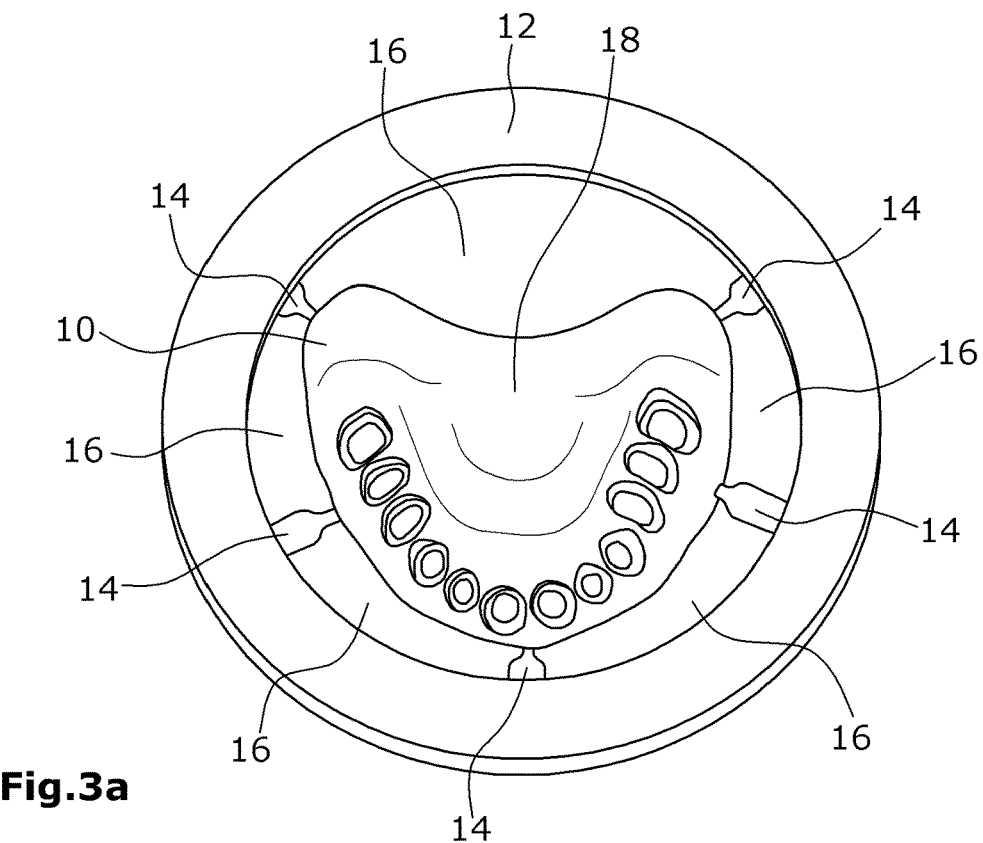
FIG. 3a illustrates a third preferred embodiment of an at least partly processed prosthetic preform for an upper jaw denture.
Figure 3B:
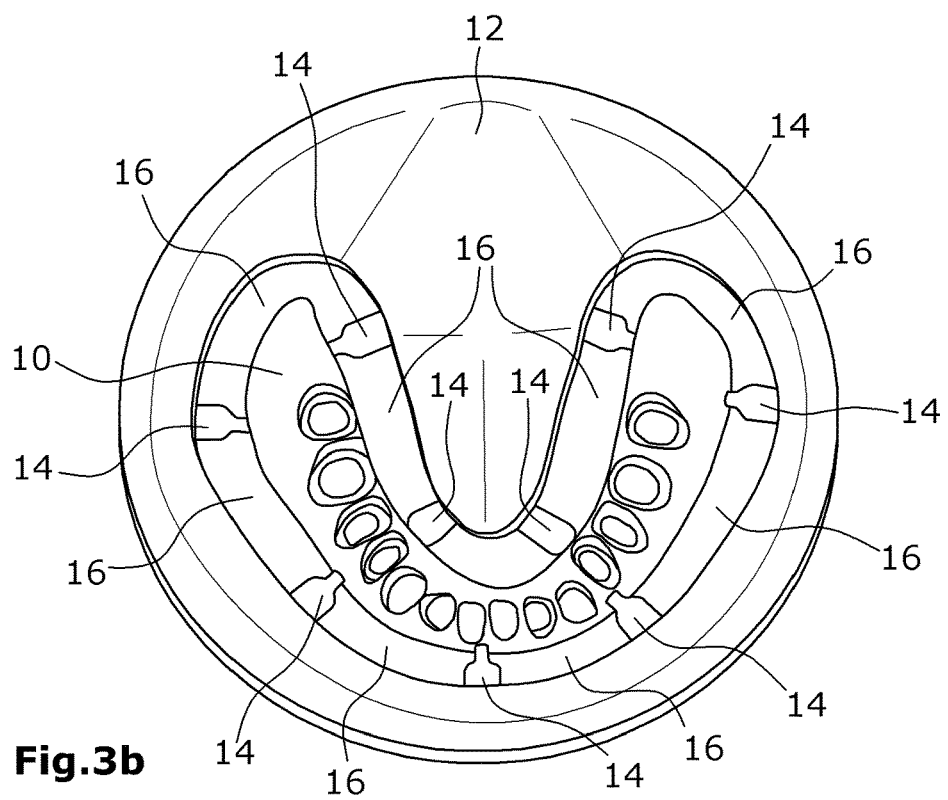
FIG. 3b illustrates a third preferred embodiment of an at least partly processed prosthetic preform for a lower jaw denture.
Figure 4A:
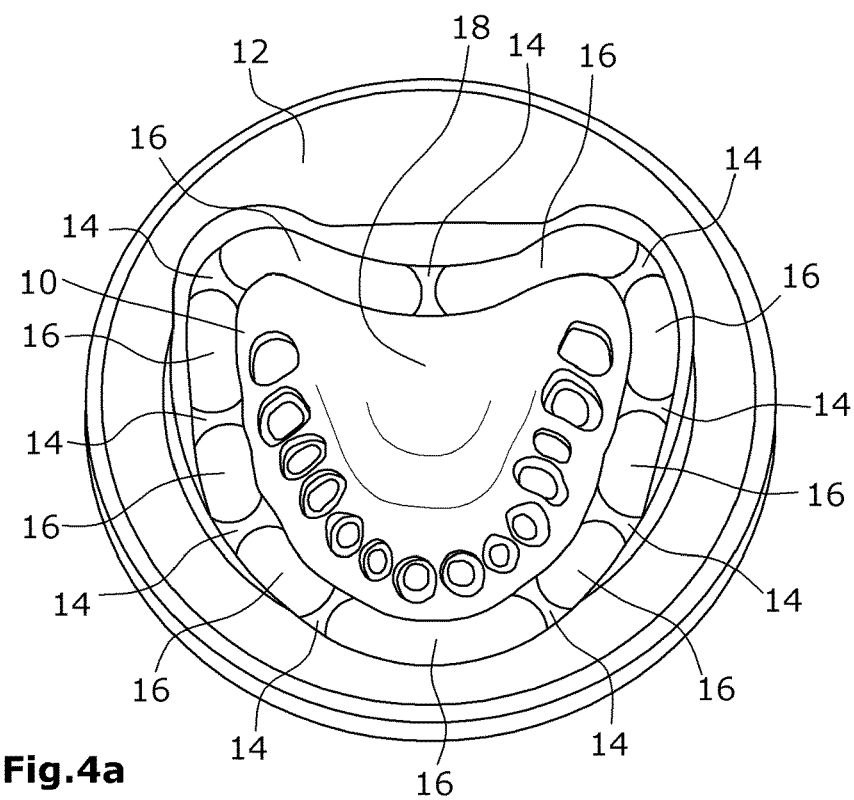
FIG. 4a illustrates a fourth preferred embodiment of an at least partly processed prosthetic preform for an upper jaw denture.
Figure 4B:
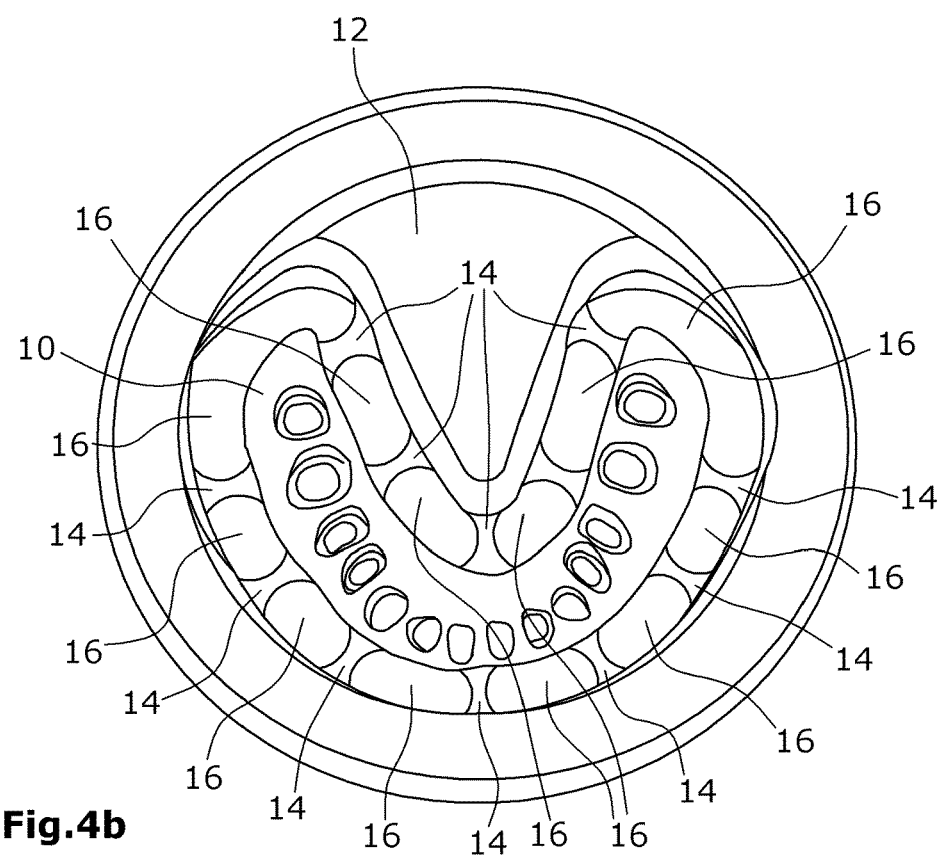
FIG. 4b illustrates a fourth preferred embodiment of an at least partly processed prosthetic preform for a lower jaw denture.

The embodiments of the at least partly processed prosthetic preforms illustrated each have a main body 10, as well as a retaining body 12 surrounding the main body 10. Here, the respective retaining body 12 is substantially annular in shape and has a circular outer contour. The height of the retaining body 12 corresponds, for example, to the height of the main bodies 10 or is even greater (FIGS. 1 and 2). Likewise, the retaining body 12 may be of a low flat shape and thus have a height smaller than the height of the main body (FIGS. 3 and 4).

The retaining body 12 is respectively connected with the main body 10 via webs 14. Continuous intermediate spaces 16 are thus formed between the webs 14, so that side faces of the main body 10 can be processed in a simple manner in particular by means of milling tools or other machining tools, in particular electric and/or hydraulic tools.

By material-removing processing, e.g. by milling, the prosthetic body is produced from the main body 10.

In the embodiments illustrated the main bodies 10 are each surrounded by a recess completely surrounding the main body 10, with the recess being formed by the intermediate spaces 16.

In a preferred embodiment, the webs 14 are always designed such that they taper from the retaining body 12 towards the main body 10. Here, the tapering may also take a stepped form. This is advantageous in that the connecting surfaces between the webs 14 and the main bodies 10 are very small. After the production of the prosthetic body from the main bodies 10, the latter are cut from the prosthetic preform by severing the webs 14, with a slight postprocessing being performed thereafter in the regions of the connecting sites between the webs 14 and the main bodies 10.

In the embodiments for producing the prosthetic bodies for upper jaws, as illustrated (Figs. a), a palate contact element 18 is formed within the substantially U-shaped main body 10.

Figure 2A:
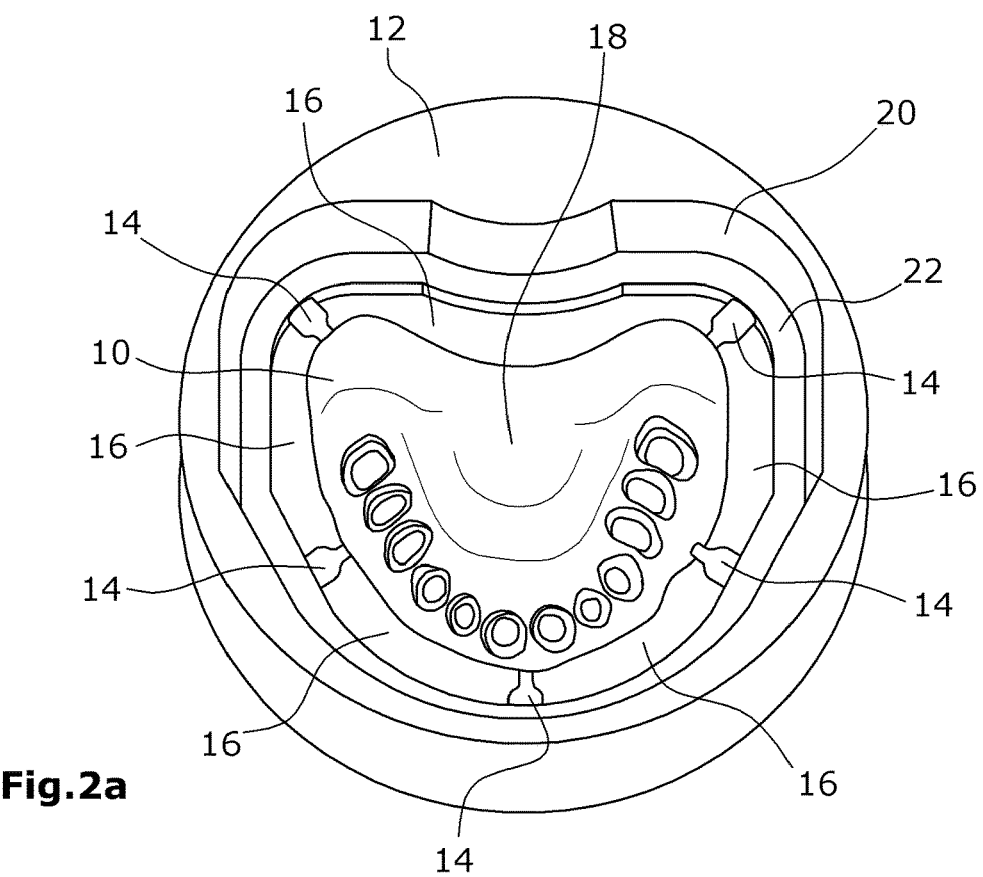
FIG. 2a illustrates a second preferred embodiment of an at least partly processed prosthetic preform for an upper jaw denture.
Figure 2B:
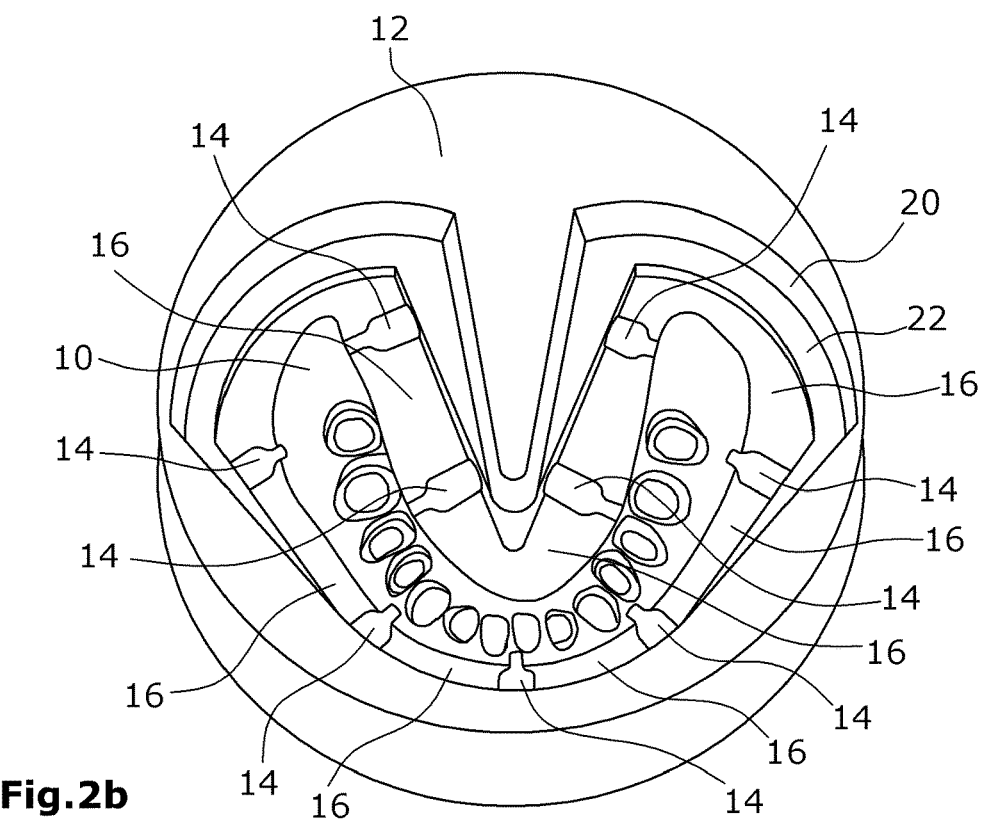
FIG. 2b illustrates a second preferred embodiment of an at least partly processed prosthetic preform for a lower jaw denture.

For a further saving of material and to improve the accessibility for the processing tool, the retaining bodies 12 in the embodiments shown in FIGS. 2a and 2b additionally have a step 20 so that a flat frame-shaped element 22 is formed which is connected with the webs 14.

As illustrated in the embodiments in FIGS. 1 to 3, the webs 14 may have generally round, possibly stepped cross sections, but may as well be designed as flat webs corresponding to the embodiment shown in FIG. 4.

The embodiment illustrated in FIG. 1 specifically has the advantage that the main body 10 remains in the original state, whereby the effort is very little. Further, it is an advantage of this embodiment that the main body 10 is fixed by means of symmetric webs 14 that are easy to process. Since the webs 14 are formed as pins having a circular cross section, a simple removal true to contour is possible.

In the embodiment illustrated in FIG. 2 the main body 12 is provided with a symmetric edge geometry. This allows for a simple automation by means of algorithms. Moreover, this embodiment additionally has the advantages of the embodiment illustrated in FIG. 1.

In the particularly preferred embodiment illustrated in FIG. 3 the main body 10 is arranged in a reduced retaining body 12. Further, this embodiment has an extremely low amount of material used, in particular because of the flat annular retaining body 12. Thereby, the production time is significantly reduced, since extremely little material is removed. This further allows for a significant saving of material as compared with circularly cylindrical round blanks.

The embodiment illustrated in FIG. 4 shows an advantageous design of the webs 14. Due to their flat design, the same can be removed in a simple manner true to contour after production.

Figure 5A:
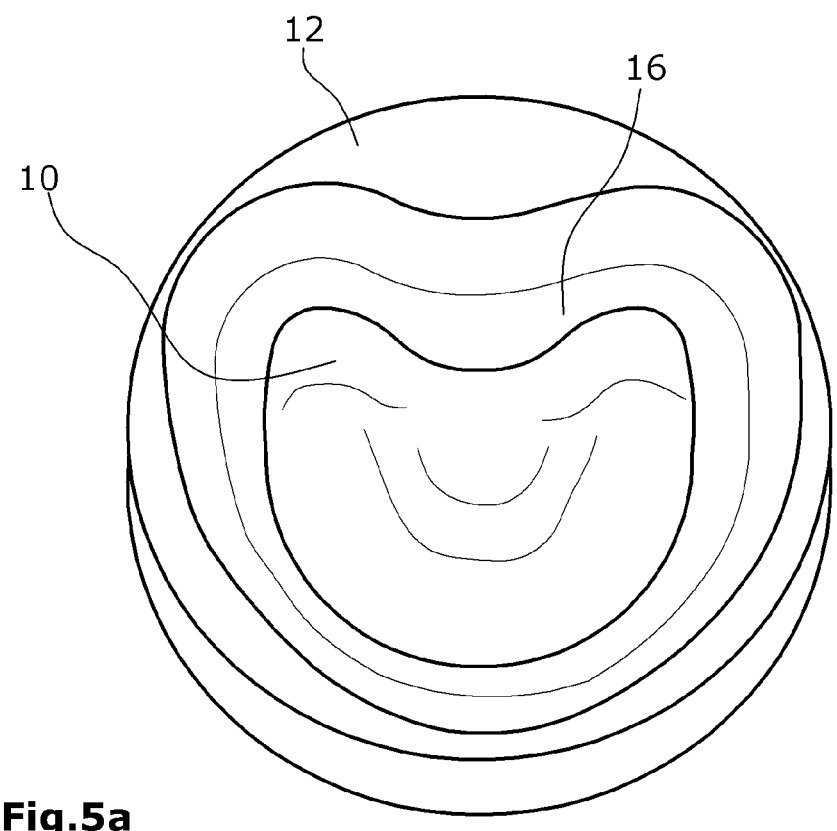
FIG. 5a illustrates a preferred embodiment of an unprocessed prosthetic preform of the present disclosure for an upper jaw denture.
Figure 5B:
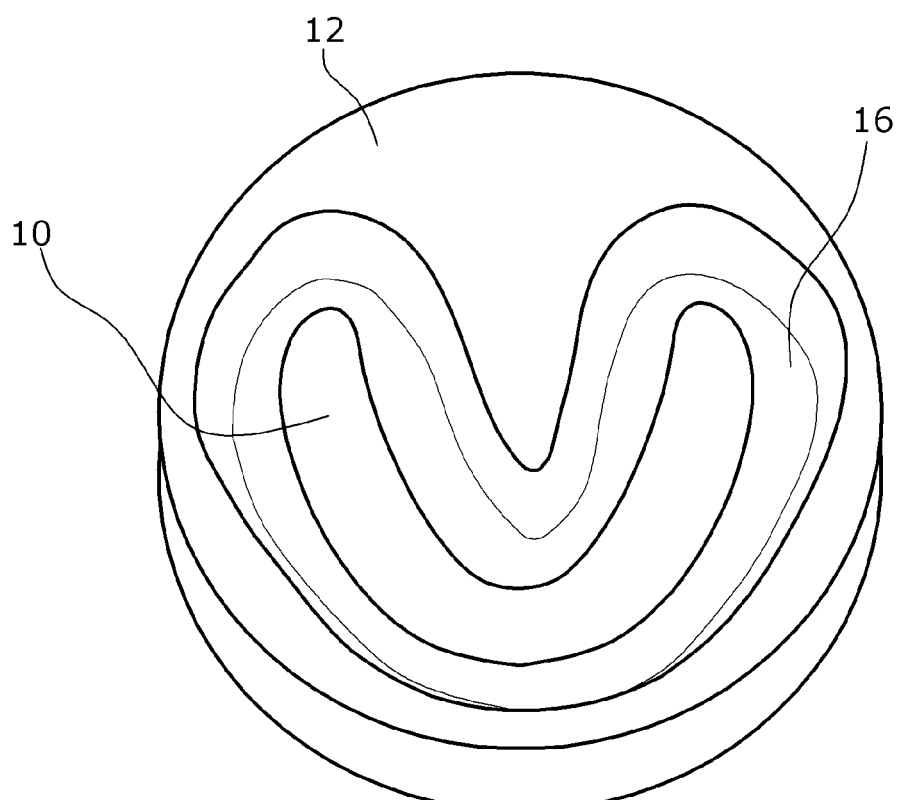
FIG. 5b illustrates a preferred embodiment of an unprocessed prosthetic preform of the present disclosure for a lower jaw denture.

In FIGS. 5a and 5b, prosthetic preforms for an upper jaw denture (FIG. 5a) and a lower jaw denture (FIG. 5b) are illustrated. These are prosthetic preforms designed according to the disclosure, which, different from the embodiments illustrated in FIGS. 1-4, have not been processed yet. With respect to circularly cylindrical round blanks, there is a difference essential to the disclosure, namely that recesses or indentations 16 are provided to form the prosthetic preforms 10. Later, openings 16, as visible in FIGS. 1-4, are formed from the recesses 16, e.g. by milling.

All preferred embodiments have the advantage essential to the disclosure that the main body 10 is already very similar to the finished part and that, for this reason, hardly any loss of material is necessary. Accordingly, it is an essential advantage of the disclosure that significant savings of material can be achieved.

The invention claimed is:

1. A dental prosthetic preform for producing a dental prosthetic body configured to receive teeth, wherein the prosthetic preform comprises polyamide, polyacrylate, polycarbonate, polyepoxy and/or polyetherketone, all with or without fillers, wherein the dental prosthetic preform has no teeth and has a positive shape approximating the shape of the dental prosthetic body, wherein the dental prosthetic preform has a main body which forms the dental prosthetic body, and wherein the main body is at least partly surrounded by a retaining body.

2. The dental prosthetic preform of claim 1, wherein the prosthetic preform comprises at least 20% less material than a cylindrical prosthetic preform.

3. The dental prosthetic preform of claim 2, wherein the prosthetic preform comprises at least 30% less material than the cylindrical prosthetic preform.

4. The dental prosthetic preform of claim 1, wherein the dental prosthetic preform has a material volume of less than 200 cm$^3$.

5. The dental prosthetic preform of claim 1, wherein the dental prosthetic preform has a circularly cylindrical basic shape, the at least one end face thereof being provided with at least one recess.

6. The dental prosthetic preform of claim 5, wherein the at least one recess surrounds the main body.

7. The dental prosthetic preform of claim 6, wherein the main body is surrounded by an annular retaining body.

8. The dental prosthetic preform of claim 7, wherein the main body is connected with the annular retaining body via webs.

9. The dental prosthetic preform of claim 6, wherein the main body substantially U-shaped.

10. The dental prosthetic preform of claim 6, wherein the main body is substantially U-shaped with an interposed palate contact element.

11. The dental prosthetic preform of claim 7, wherein the annular retaining body is at least as high as the main body.

12. The dental prosthetic preform of claim 7, wherein the annular retaining body is flat and is of a lesser height than the main body.

13. The dental prosthetic preform of claim 3, wherein the prosthetic preform comprises at least 40% less material than the cylindrical prosthetic preform.

14. The dental prosthetic preform of claim 13, wherein the prosthetic preform comprises at least 50% less material than the cylindrical prosthetic preform.

15. The dental prosthetic preform of claim 4, wherein the dental prosthetic preform has a material volume of less than 180 cm$^3$.

16. The dental prosthetic preform of claim 15, wherein the dental prosthetic preform has a material volume of less than 150 cm$^3$.

17. The dental prosthetic preform of claim 16, wherein the dental prosthetic preform has a material volume of less than 125 cm$^3$.

18. A dental prosthetic preform for producing a dental prosthetic body to receive teeth, comprising:
a main body which forms the dental prosthetic body, the main body having no teeth and having a tooth receiving region configured to receive the teeth;
a retaining body at least partially surrounding the main body; and
a plurality of webs connecting the main body and the retaining body to one another such that at least one intermediate space surrounds the main body,
wherein the main body, retaining body, and the plurality of webs comprises a material selected from the group consisting of polyamide, polyacrylate, polycarbonate, polyepoxy, polyetherketone, and combinations thereof.

* * * * *